United States Patent [19] [11] 3,952,315
Cecco [45] Apr. 20, 1976

[54] EDDY CURRENT DISCONTINUITY PROBE UTILIZING A PERMANENT MAGNET BOBBIN WITH AT LEAST ONE A.C. ENERGIZED COIL MOUNTED IN A GROOVE THEREON

[75] Inventor: Valentino S. Cecco, Deep River, Canada

[73] Assignee: Atomic Energy of Canada Limited, Ottawa, Canada

[22] Filed: July 29, 1974

[21] Appl. No.: 492,457

[30] Foreign Application Priority Data
Oct. 15, 1973 Canada .............................. 183404

[52] U.S. Cl. ................................................ 324/37
[51] Int. Cl.² ........................................ G01R 33/12
[58] Field of Search ................................ 324/37, 40

[56] References Cited
UNITED STATES PATENTS
2,955,253  10/1960  Bryant et al. ..................... 324/37
2,964,699  12/1960  Perriam et al. .................... 324/37

FOREIGN PATENTS OR APPLICATIONS
226,040  3/1959  Australia ............................ 324/37
1,231,641  5/1971  United Kingdom .................. 324/37
766,353  1/1957  United Kingdom .................. 324/40
936,033  9/1963  United Kingdom .................. 324/40

Primary Examiner—Robert J. Corcoran
Attorney, Agent, or Firm—Edward Rymek

[57] ABSTRACT

Eddy-current inspection for cracks, flaws, etc, in rails, rods, etc. is conventional. For ferromagnetic material structures, it is found to be advantageous to magnetically saturate the material during inspection. The inventive eddy current probe facilitates the inspection of ferromagnetic tubing by saturating the tubing from within and only in the region of the test coils. Inspection may therefore be carried out on tubing which is installed in systems such as steam generators. The probe includes a bobbin on which test coils are wound. The bobbin may consist of a permanent magnet having a field of sufficient stength to provide the necessary magnetic saturation, or the field may be supplemented by driving a direct current through one or more of the coils. In a third embodiment, the bobbin may be made from high $\mu$ material and the entire saturating field is provided by driving a direct current either through the test coils or through additional dc bias coils located on the bobbin.

5 Claims, 11 Drawing Figures

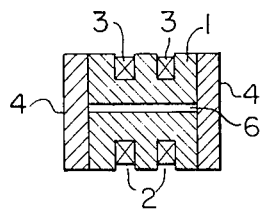
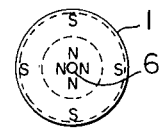
FIG.4a  FIG.4b
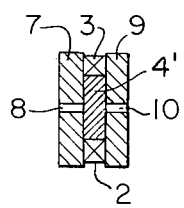
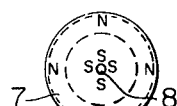
FIG.5a  FIG.5b  FIG.5c
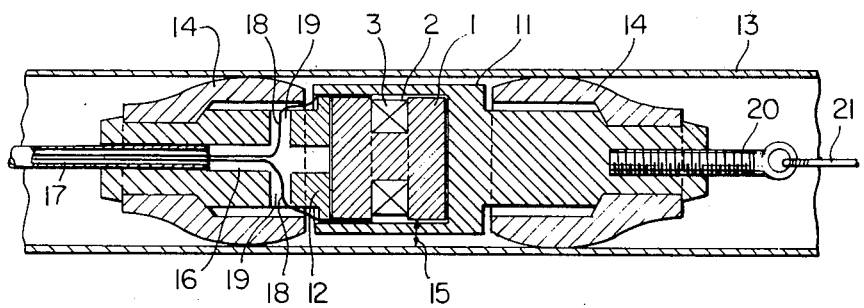
FIG.6

EDDY CURRENT DISCONTINUITY PROBE UTILIZING A PERMANENT MAGNET BOBBIN WITH AT LEAST ONE A.C. ENERGIZED COIL MOUNTED IN A GROOVE THEREON

This invention is directed to a novel eddy current probe for inspecting ferromagnetic materials and in particular, to a probe which may be used to effectively inspect tubing and the like, which is located in complex installations such as steam generators.

Eddy current testing has been found to be a very useful tool in the detection of cracks, flaws, etc. in various structures, such as, rails, rods, tubes, and even composite workpieces. Several conventional eddy current inspection techniques have evolved, such as, the absolute and the differential coil techniques with their associated electronics. In the differential coil technique, the coils in the probe may be used as induction coils where change in inductance is measured, or as coupling coils with an excitation and pick-up coil. It has also been determined that magnetic materials can be satisfactorily inspected by magnetically saturating the region under inspection to eliminate the large permeability variations which occur. Many systems have been devised for inspecting tubing either as it is being manufactured, or just prior to assembly into a complex structure. Some examples of such systems are described in U.S. Pat. No. 3,271,664 issued to J. M. Mountz et al. on Sept. 6, 1966, and assigned to Magnaflux Corporation and U.S. Pat. No. 3,526,829 issued to G. A. Noble on Sept. 1, 1970 and assigned to Chrysler Corporation. However, these systems suffer from one major disadvantage since they provide for the saturating magnetic field to be applied to the exterior of the tubing by a large permanent magnet or electromagnet. Thus, they are unable to effectively test the tubing after it has been installed in a complex structure. or after the tubing has been in use in such a structure. Periodic in-service inspections are necessary to prevent costly breakdowns during the operation of a system, such as a steam generator, and also to provide valuable test results for the design and maintenance of such systems. It is therefore desireable to have an inspection system in which the probe may be drawn through the interior of the tubing at a predetermined rate to detect flaws, cracks, or wear. One such probe is described in U.S. Pat. No. 2,964,699 issued to J. T. Perrian et al., and assigned to Imperial Chemical Industries Limited. However, this probe does not provide a saturating magnetic field of sufficient concentration or strength to provide effective inspection of magnetic or weakly magnetic tubing because of the magnet configuration and materials used in the probe housing. In addition, it does not provide for a versatile probe which is capable of inspecting tubing having different thicknesses since the magnetic field cannot be varied.

It is, therefore, an object of this invention to provide an improved eddy current probe for the inspection of tubing made from magnetic or weakly magnetic materials.

It is a further object of this invention to provide a probe which will concentrate the saturating magnetic field over a small area of the tubing in the vicinity of the probe coils.

It is yet another object of this invention to provide a probe which can develop a magnetic field of sufficient strength to achieve local saturation of the tubing material in the vicinity of the probe coils.

These and other objects are achieved by providing a permanent magnet bobbin having one or more symmetrically spaced test coil grooves. The magnetic field is intended to saturate the portion of the tubing in the vicinity of the test coils. The bobbin may be magnetized axially, radially, or diametrically. The probe may further include magnetic keepers made of high magnetic permeability ($\mu$) material to increase the field density. The bobbin, and/or keepers, are rigidly held in a probe housing made of non-conducting or high electrical resistivity material. The housing includes guides which maintain constant the gap or clearance between the bobbin and the tubing inner wall, as the probe is moved through the tubing. The probe further includes a shielded conductor cable, embedded in one end of the probe housing with leads connected to the coils.

In another embodiment, further coils may be placed in grooves in the bobbin through which d.c. is made to flow to increase the magnetic field provided by the permanent magnet.

In yet another embodiment, the test coil or coils may be adapted to carry the d.c. in addition to the a.c. test signals.

In another embodiment, the bobbin may be made of a high magnetic permeability ($\mu$), high electrical resistivity metal with test coils in inner grooves, and further coils in outer grooves adapted to carry d.c. bias currents.

In yet another embodiment, the test coil or coils in the bobbins may be adapted to carry both the a.c. test signals and the d.c. bias.

In the drawings:

FIGS. 4a and 4b are a cross-section and an end view respectively of a radially magnetized permanent magnet bobbin;

Figure 7A:
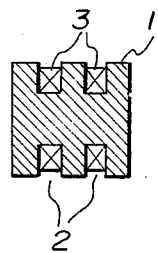
Figure 7B:
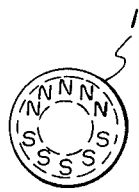

FIGS. 5a, 5b, and 5c are a cross-section, and end views respectively, of a second form of radially magnetized permanent magnet bobbin;

FIG. 6 is a cross-section of one particular eddy current probe embodying the invention and FIGS. 7a and 7b are a cross-section and an end view respectively of a diametrically magnetized permanent magnet bobbin.

According to the invention, the saturating magnetic field, required for the inspection of magnetic or weakly magnetic tubing, may be created by a permanent magnet, a d.c. electromagnet, or a combination of both. As illustrated in FIGS. 1 to 5, this saturating field is provided by a cylindrical bobbin 1, having one or more grooves 2, in which one or more test coil windings 3, are located.

Figure 1:
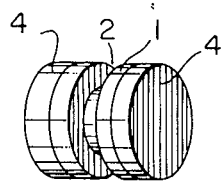
FIG. 1 is a perspective view of a bobbin having a single groove.
Figure 2:
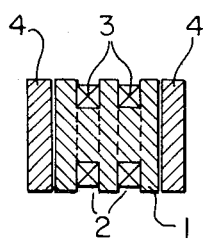
FIG. 2 is a cross-section of a bobbin having two grooves for test coils.

In the cases where permanent magnets are preferred, the bobbins 1, are constructed from permanent magnet materials such as Alnico 5, Alnico 8, Barium Ferrite, or a rare earth-cobalt alloy such as Pt-Co. In addition, magnetic keepers 4, made from a high $\mu$ material, may be placed in intimate contact with the ends of the bobbin as shown in FIGS. 1, 2 and 4a to provide a low reluctance path for the magnetic field.

In the cases where electro-magnets are preferred, the bobbins are constructed from materials such as mild steel, ferrite, or any high $\mu$, high electrical resistivity metal.

The bobbins may have various configurations. For bobbins, such as illustrated in FIGS. 1 and 2, either permanent or electromagnet bobbins may have one or more grooves 2, wherein the test coils 3, are located. These coils may carry only a.c. signals or they may also have a d.c. component flowing through them. Thus, the bobbin may provide a permanent magnet saturating field, an electromagnet saturating field, or a combination of both.

Figure 3:
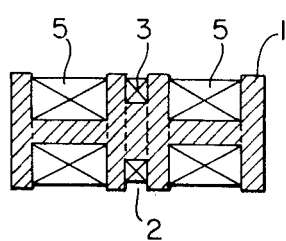
FIG. 3 is a cross-section of a bobbin having a single groove for test coils with additional grooves for saturation coils.

FIG. 3 illustrates a bobbin 1, which includes coils 5 for direct saturation currents, in addition to test coils 3. This arrangement may be used either as a purely electromagnetic probe, or as a combination probe if the bobbin is a permanent magnet.

Generally, for permanent magnet or combination probes, the bobbin is magnetized axially. However, for permanent magnet probes, the bobbin may also be magnetized radially or diametrically. FIG. 4a illustrates one embodiment of a bobbin which is magnetized radially. The bobbin is constructed of permanent magnet material, as described above, with one or more grooves 2, in which the test coils 3, are set. In addition, a cylindrical perforation 6, along the axis of the bobbin is required. The bobbin may be magnetized with the south pole at the circumferencial edge, as shown in FIG. 4b, or with the north pole at the circumferential edge. It is preferred to use magnetic keepers with this bobbin to provide a low reluctance return path for the magnetic field.

FIG. 5a illustrates a second bobbin which is radially magnetized. In this embodiment, the bobbin consists of a first disc 7, with a perforation 8 at its center, and magnetized such that the north pole is at its circumferential edge. (FIG. 5b), and a second disc 9, with a hole 10 at its center, and magnetized such that the south pole is at its circumferencial edge (FIG. 5c). The two discs, 7 and 9, are joined by a magnetic keeper 4', which has a radius smaller then the radius of the discs forming the groove for the test coils 3. Additional disc magnets spaced by magnetic keepers may be joined to the above bobbin if desired, with adjacent discs being of opposite polarity.

FIG. 7a illustrates one embodiment of a bobbin which is magnetized diametrically. The bobbin 1 is constructed of permanent magnet material, as described above, with one or more grooves 2 in which the test coils 3 are set. The bobbin is magnetized with the south pole along one half of the circumferencial edge and the north pole along the other half of the circumferential edge, as shown in FIG. 7b.

Test coils 3, as well as electromagnet coils 5, (FIG. 3), may be made from copper wire commonly called magnet wire. However, if low carbon mild steel wire is used for all windings or for the inner windings of each coil, the magnetic field may be strengthened since they provide a lower reluctance path than the copper wire.

To form an eddy current probe, the bobbin is rigidly held in a probe housing made of any non-conducting or high electrical resistivity material which will not interfere with the magnetic field, and will protect the bobbin and winding as they move through a tubing. This structure will usually include guides or fingers which allow the probe to have a constant predetermined clearance between the bobbin and the tubing inner wall as the probe is moved through the tubing. FIG. 6 illustrates one example of a probe structure embodying the invention.

For simplicity, the bobbin 1, illustrated in FIG. 1, is shown in the example probe. The bobbin 1 is rigidly fixed in a probe housing — including a front probe former 11, and a rear probe former 12; these are made of any non-conducting or high electrical resistivity material such as non-magnetic stainless steel or Zircalloy 2. The front probe former 11 is shown to envelop the bobbin, however, this need not be the case. The housing must have sufficient strength so that it will not deform or break as the probe is pulled or pushed through the tubing 13. Cup shaped quides 14, are mounted on the front and rear former 11 and 12, so as to center the probe within the tubing 13, maintaining a constant predetermined gap or clearance 15 between the bobbin circumference, and the inner wall of tubing 13. In most cases, a clearance 15, of about 0.020 inches, provides satisfactory operation of the probe. However, it is to be noted that the gap should be as small as practically possible. The rear former 12, has an opening 16 along the axis of the former, into which a shielded cable 17 is inserted and connected to coil leads 18 which emerge from the bobbin 1 and enter into the rear former 12 through one or more openings 19. Finally a puller hook 20 is shown embedded or threaded in the front former 11 by which the probe may be pulled through tubing 13 by a wire 21. In operation, the unidirectional magnetic field should be as large as possible, for example, Monel 400 tubing requires a magnetic field intensity of 100–500 oersteds. In embodiments where electromagnets are used to provide the unidirectional field in whole, or in part, the d.c. may be driven through separate coils or through the test coils. However, in any case, the a.c. signal should be equal to approximately 10–20% of the d.c. If the a.c. signal is too high, the tubing will not remain saturated at all times, whereas, if the a.c. signal is too low, the signal-to-noise ratio will suffer.

In addition, it has been found that the length-to-diameter ratio of the bobbin should be as large as possible with a minimum L/D ratio of 0.5. However, if the bobbin is too long, a large area of the tubing wall must be saturated. For large diameter tubes as well as tubes with small U bends, the L/D ratio will be kept close to the minimum.

Eddy current probes incorporating the invention, have been found to provide improved test results over prior art eddy current probes, and features on the tubing such as grooves, holes, flats, or baffle plates were easily identified since the probe provided a high signal-to-noise ratio.

As a further application of the system described wherein the saturating field is provided by a magnet within the probe, the probe may be used to test large diameter tubing from the inside or outside, or flat surfaces by eliminating the front probe former 11 (FIG. 6) and the magnet keeper 4 at the front end of the bobbin 1. The probe may then be used as a surface probe with the front end of the bobbin 1 making contact with surface of the material to be tested.

What is claimed is:

1. An eddy-current probe for the detection of discontinuities in a magnetic or weakly magnetic tubing from within the tubing comprising:
    probe housing means of non-conducting or high electrical resistivity material;

a permanent magnet cyclindrical bobbin rigidly mounted within said housing to provide an unidirectional magnetic field for saturating the tubing adjacent said bobbin; said bobbin having at least one groove symmetrically located on the circumferential surface of the bobbin;

at least one test coil wound on the bobbin within the groove, said one coil adapted to be connected to an alternating current source to generate eddy currents within said tubing and further adapted to be connected to a d.c. source to produce a magnetic field to supplement said unidirectional magnetic field.

2. An eddy-current probe for the detection of discontinuities in a magnetic or weakly magnetic tubing from within the tubing comprising:

probe housing means of non-conducting or high electrical resistivity material;

a permanent magnet cylindrical bobbin rigidly mounted within said housing to provide a unidirectional magnetic field for saturating the tubing adjacent said bobbin, said bobbin having at least one first groove symmetrically located on the circumferential surface of the bobbin and two further grooves symmetrically located on the circumferential surface at the outer ends of the bobbin;

at least one test coil wound on the bobbin within the first groove, said one coil adapted to be connected to an alternating current source to generate eddy currents within said tubing; and a d.c. coil wound on the bobbin within each of the outer grooves and adapted to be connected to a d.c. source to produce a magnetic field to supplement said unidirectional magnetic field.

3. An eddy-current probe for the detection of discontinuities in a magnetic or weakly magnetic tubing from within the tubing comrising:

probe housing means of non-conducting or high electrical resistivity material;

a permanent magnet cylindrical bobbin having an axially located cylindrical perforation, said bobbin being radially magnetized and rigidly mounted within said housing to provide a unidirectional magnetic field for saturating the tubing adjacent said bobbin, said bobbin having at least one groove symmetrically located on the circumferential surface of the bobbin;

at least one test coil wound on the bobbin within the groove, said one coil adapted to be connected to an alternating current source to generate eddy currents within said tubing.

4. An eddy-current probe for the detection of discontinuities in a magnetic or weakly magnetic tubing from within the tubing comprising:

probe housing means of non-conducting or high electrical resistivity material;

a permanent magnet cylyndrical bobbin rigidly mounted within said housing to provide a unidirectional magnetic field for saturating the tubing adjacent said bobbin, said bobbin including two cylindrical discs of radius $r$ with axial perforations, the discs being radially magnetized permanent magnets of opposite polarity, and a cylindrical magnetic keeper of high $\mu$ material and of radius less than $r$, symmetrically fixed between said two disc magnets to form a symmetrical groove on the circumferential surface of the bobbin;

at least one test coil wound on the bobbin within the groove, said one coil adapted to be connected to an alternating current source to generate eddy currents within said tubing.

5. An eddy-current probe for the detection of discontinuities in a magnetic or weakly magnetic tubing from within the tubing comprising:

probe housing means of non-conducting or high electrical resistivity material;

a diametrically magnetized permanent magnet cylindrical bobbin rigidly mounted within said housing to provide a unidirectional magnetic field for saturating the tubing adjacent said bobbin, said bobbin having at least one one groove symmetrically located on the circumferential surface of the bobbin;

at least one test coil wound on the bobbin within the groove, said one coil adapted to be connected to an alternating current source to generate eddy currents within said tubing.

* * * * *